United States Patent
Chmielewski et al.

(10) Patent No.: US 10,688,192 B2
(45) Date of Patent: Jun. 23, 2020

(54) CLEAVABLE CONJUGATES OF ANTIBIOTICS AND AN ANTIBACTERIAL CELL-PENETRATING PEPTIDE

(71) Applicant: Purdue Research Foundation, West Lafayette, IN (US)

(72) Inventors: Jean Anne Chmielewski, West Lafayette, IN (US); Mohamed Seleem, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 4 days.

(21) Appl. No.: 16/280,093

(22) Filed: Feb. 20, 2019

(65) Prior Publication Data

US 2019/0175741 A1    Jun. 13, 2019

Related U.S. Application Data

(63) Continuation of application No. 16/050,472, filed on Jul. 31, 2018, now Pat. No. 10,265,408.

(60) Provisional application No. 62/539,570, filed on Aug. 1, 2017.

(51) Int. Cl.
*A61K 47/61* (2017.01)
*A61K 47/55* (2017.01)
*A61K 47/65* (2017.01)
*A61K 31/7048* (2006.01)
*A61K 31/395* (2006.01)
*A61K 31/7036* (2006.01)
*A61K 47/64* (2017.01)

(52) U.S. Cl.
CPC .......... *A61K 47/552* (2017.08); *A61K 31/395* (2013.01); *A61K 31/7036* (2013.01); *A61K 31/7048* (2013.01); *A61K 47/61* (2017.08); *A61K 47/64* (2017.08); *A61K 47/65* (2017.08)

(58) Field of Classification Search
CPC .............. A61K 47/552; A61K 31/7036; A61K 31/395; A61K 47/65; A61K 47/61; A61K 31/7048
See application file for complete search history.

(56) References Cited

U.S. PATENT DOCUMENTS 10,265,408 B2 *    4/2019    Chmielewski ....... A61K 47/552

OTHER PUBLICATIONS

Anna Brezden, etc., Dual targeting of intracellular pathogenic bacteria with a cleavable conjugate of kanamycin and an antibacterial cell-penetrating peptide, J. Am. Chem. Soc., 2016, 138, 10945-10949.

* cited by examiner

*Primary Examiner* — Sudhakar Katakam
(74) *Attorney, Agent, or Firm* — Purdue Research Foundation; Zhigang Rao

(57) ABSTRACT

The present disclosure relates to novel cleavable conjugates of antibiotics and an antibacterial cell-penetrating peptide, and methods to make and use the novel cleavable conjugates of antibiotics and an antibacterial cell-penetrating peptide.

14 Claims, No Drawings

CLEAVABLE CONJUGATES OF ANTIBIOTICS AND AN ANTIBACTERIAL CELL-PENETRATING PEPTIDE

CROSS-REFERENCE TO RELATED APPLICATION

This application is a continuation application of U.S. patent application Ser. No. 16/050,472 filed Jul. 31, 2018, which is related to and claims the benefits of U.S. Provisional Application Ser. No. 62/539,570, filed Aug. 1, 2017, the contents of which are incorporated herein entirely.

GOVERNMENT RIGHTS

This invention was made with government support under CHE1012316 awarded by the National Science Foundation. The United States government has certain rights in the invention.

STATEMENT REGARDING PRIOR DISCLOSURES BY THE INVENTORS OR JOINT INVENTORS UNDER 37 C.F.R. 1.77(B)(6)

Jean A. Chmielewski and Mohamed Seleem, the inventors or joint inventors of the present disclosure, publicly disclosed information related to the present disclosure in article Anna Brezden, etc., Dual targeting of intracellular pathogenic bacteria with a cleavable conjugate of kanamycin and an antibacterial cell-penetrating peptide, J. Am. Chem. Soc., 2016, 138, 10945-10949. The article was first published online on Aug. 5, 2016, which is less than one year from the filing date of the U.S. Provisional Application Ser. No. 62/539,570, filed Aug. 1, 2017. The other five listed co-authors Anna Brezden, Mohamed F. Mohamed, Manish Nepal, John S. Harwood, and Jerrin Kuriakose of the article are not inventors for the present disclosure because the five listed co-authors only provided supervised contributions instead of providing inventive contribution. A copy of a print out of the article is provided on a concurrently filed Information Disclosure Statement (IDS).

TECHNICAL FIELD

The present disclosure relates to novel cleavable conjugates of antibiotics and an antibacterial cell-penetrating peptide, and methods to make and use the novel cleavable conjugates of antibiotics and an antibacterial cell-penetrating peptide.

BACKGROUND

This section introduces aspects that may help facilitate a better understanding of the disclosure. Accordingly, these statements are to be read in this light and are not to be understood as admissions about what is or is not prior art.

The emergence of antibiotic resistance is a notorious problem worldwide. In the United States alone, antibiotic-resistant bacteria infect at least two million people, killing 23,000 patients annually. Currently, members of the ESKAPE pathogens (*Enterococcus faecium, Staphylococcus aureus, Klebsiella pneumoniae, Acinetobacter baumannii, Pseudomonas aeruginosa,* and *Enterobacter* species) represent one of the most significant threats to human health as strains exhibit resistance to multiple antibiotic classes. Compounding the situation further, global reports of extensively drug-resistant (XDR) and pandrug-resistant (PDR) isolates of *P. aeruginosa* and *A. baumannii* have been increasing. The ability of these resistant pathogens to form biofilms that are highly tolerant to antibiotics further aggravates the situation, ultimately leading to persistent and recurring infections.

Aminoglycosides are a class of valuable antibiotics that are used in the treatment of several microbial infections. Aminoglycosides bind to the 16S rRNA component of the bacterial ribosome, leading to mistranslation and bacterial death. However, the worldwide epidemic of resistance to aminoglycosides, to kanamycin in particular, has diminished their widespread clinical use.

Hence, the development of therapeutic alternatives that have novel mechanisms of action are urgently needed in order to effectively address this problem.

SUMMARY

The present invention provides novel cleavable conjugates of antibiotics and an antibacterial cell-penetrating peptide that may provide novel mechanisms of action to better address the antibiotic resistance issue. Specifically, the novel cleavable conjugates of antibiotics and an antibacterial cell-penetrating peptide of the present disclosure are represented in the formula below:

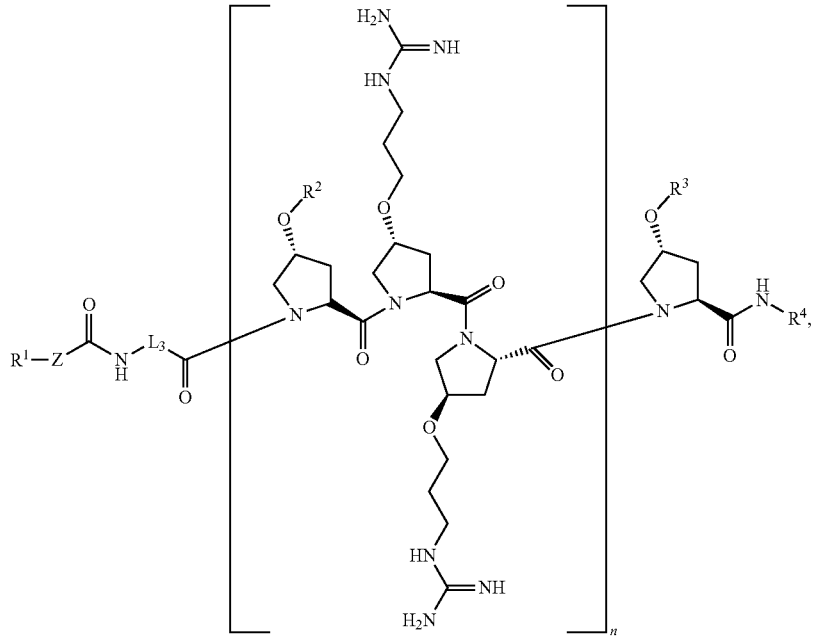

or a stereoisomer, tautomer, solvate, pharmaceutically acceptable salt, derivative or prodrug thereof, wherein $R^1$ is an antibiotic moiety;

$R^2$ and $R^3$ are each independently H, a $C_1$-$C_8$ branched or unbranched alkyl chain, or a $C_3$-$C_8$ cyclic alkyl;

$R^4$ is H, a $C_1$-$C_8$ branched or unbranched alkyl chain, or a $C_3$-$C_8$ cyclic alkyl;

$L_3$ is $C_1$-$C_8$ branched or unbranched alkyl chain, or a $C_3$-$C_8$ cyclic alkyl;

Z is a linker comprising a disulfide bond (S—S bond); and n is 3-8.

In one embodiment, the present disclosure provides methods for treating a patient, either mammal or animal, having a microbial infection with the presently disclosed novel cleavable conjugates of antibiotics and an antibacterial cell-penetrating peptide, or a stereoisomer, tautomer, solvate, pharmaceutically acceptable salt, derivative or prodrug thereof.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

As used herein, the term "salts" and/or "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

As used herein, the term "nitrogen-protecting group" in the present disclosure may be any functional group that can make the amine nitrogen to be protected as any form of carbamate, benzyl amine, amide, thioamide, sulfonamide, urea, or thiourea. The nitrogen-protecting group may include but is not limited to benzoyl, benzyloxycarbonyl, t-butoxycarbonyl, benzene sulfonyl, toluene sulfonyl, benzyl, benzhydryl, trityl, acetyl, or trifluoroacetyl.

As used herein, the term "antibiotics" refers to any anti-bacterial antibiotics, which are antibiotics that do not have activity against viruses, fungi and other non-bacterial microbes. The anti-bacterial antibiotics include bactericidal antibiotics, which destroy bacteria, and bacteriostatic antibiotics which prevent bacteria from multiplying. The anti-bacterial antibiotics further include "narrow-spectrum" antibiotics which target particular types of bacteria, such as Gram negative or Gram-positive bacteria, and broad spectrum antibiotics which affect a wide range of bacteria. Likewise, the anti-bacterial antibiotics include antibiotics for ingestion as well as antibiotics for intravenous administration which are often used to treat serious infections such as deep-seeded systemic infections, and antibiotics for topical administration. The anti-bacterial antibiotics comprise antibiotics within the following presently recognized classes: aminoglycoside antibiotics, Ansamycins, Beta-lactam antibiotics (including the carbacephem, carbapenems, cephalosporins (first, second, third and fourth generations), monobactams and penicillins, Glycopeptides, Macrolides, lincosamides, Polypeptides, Quinolones, Sulphonamides, Tetracyclines, Cyclic lipopeptides, Glycylcyclines, Oxazolidinones, diaminopyrimidines, Nitrofurans, Rifamycins, antibiotic peptides, amphenicols, nitroimidazoles, streptogramins and phosphomycins.

As used herein, the particular term "aminoglycoside antibiotics" refers to a medicinal and bacteriologic category of traditional antibacterial therapeutic agents that inhibit protein synthesis and contain as a portion of the molecule an amino-modified glycoside (sugar). The term can also refer more generally to any organic molecule that contains amino sugar substructures. Aminoglycoside antibiotics may include but is not limited to Gentamicin, Streptomycin, Kanamycin, Fradiomyctn, Paromomycin, Tobramycin, Netilmicin, Amikacin, Neomycin, Ribostamycin, Dibekacin, Sisomicin, Isepamicin, Bekanamycin, Astromicin, Plazomicin, or any derivative thereof.

As used herein, the term "antibiotic moiety" as referred in a chemical structure refers to the structure of an antibiotic agent that is chemically linked to the structure of another chemical or partial structure of another chemical, through a chemical functional groups such as an ester group, an amide group or an acyl amide group through the hydroxyl, amino or amide group of the antibiotic agent.

The term "cleavable" means that the compound of the present disclosure can be cleaved from a disulfide bond (—S—S—).

The present invention provides novel cleavable conjugated cell penetrating peptides. Accordingly, the present invention provides a compound of Formula I:

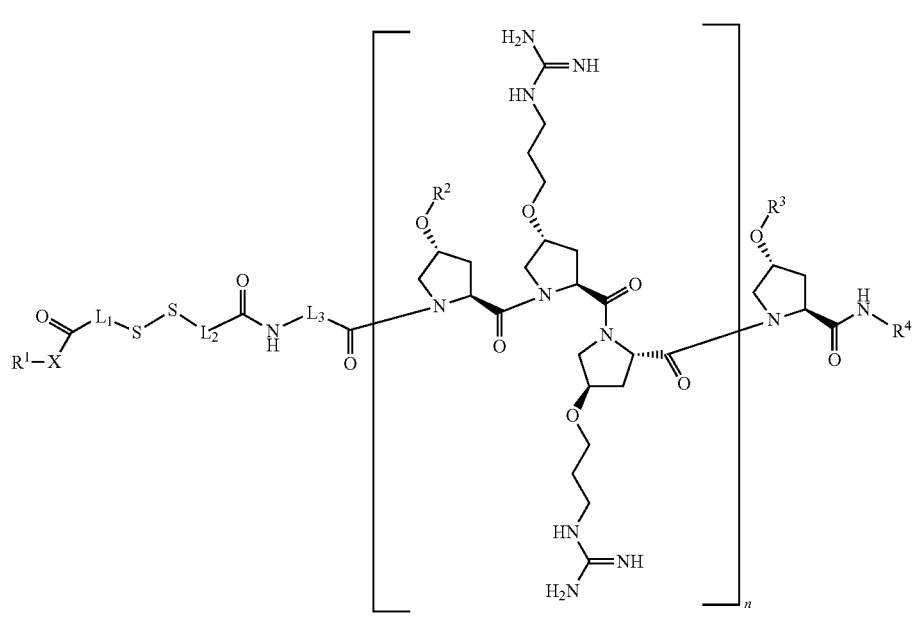

I or a stereoisomer, tautomer, solvate, pharmaceutically acceptable salt, derivative or prodrug thereof, wherein
$R^1$ is an antibiotic moiety;
$R^2$ and $R^3$ are each independently H, a $C_1$-$C_8$ branched or unbranched alkyl chain, or a $C_3$-$C_8$ cyclic alkyl;
$R^4$ is H, a $C_1$-$C_8$ branched or unbranched alkyl chain, or a $C_3$-$C_8$ cyclic alkyl;
$L_1$, $L_2$, $L_3$ are each independently $C_1$-$C_8$ branched or unbranched alkyl chain, or a $C_3$-$C_8$ cyclic alkyl;
X is O or $NR^5$, wherein $R^5$ is H, $C_1$-$C_8$ branched or unbranched alkyl chain, or a $C_3$-$C_8$ cyclic alkyl, or X combined with $R^1$ together is an antibiotic moiety; and
n is 3-8.

In one embodiment, the present invention provides a compound of Formula I, wherein $R^1$ or $R^1$—X represents the moiety of an aminoglycoside antibiotics or any derivative thereof.

In one embodiment, the present invention provides a compound of Formula I, wherein $R^1$ or $R^1$—X represents an aminoglycoside antibiotics moiety, wherein the aminoglycoside antibiotics is selected from the group consisting of Gentamicin, Streptomycin, Kanamycin, Fradiomyctn, Paromomycin, Tobramycin, Netilmicin, Amikacin, Neomycin, Ribostamycin, Dibekacin, Sisomicin, Isepamicin, Bekanamycin, Astromicin, Plazomicin, and any derivative thereof.

In one embodiment, the present invention provides a compound of Formula I, wherein $R^1$ or $R^1$—X represents Vancomycin, Linezolid, Erythromycin, Eperezolid, or any derivative thereof.

In one embodiment, the present invention provides a compound of Formula I, wherein $R^1$ or $R^1$—X represents an antibiotics moiety of an antibiotics, and wherein the antibiotics is selected from the group consisting of Gentamicin, Streptomycin, Kanamycin, Fradiomyctn, Paromomycin, Tobramycin, Netilmicin, Amikacin, Neomycin, Ribostamycin, Dibekacin, Sisomicin, Isepamicin, Bekanamycin, Astromicin, Plazomicin, Vancomycin, Linezolid, Erythromycin, Eperezolid, and any derivative thereof.

In one embodiment, the present invention provides a compound of Formula I, wherein $R^2$ and $R^3$ are each independently $C_1$-$C_4$ branched or unbranched alkyl chain.

In one embodiment, the present invention provides a compound of Formula I, wherein $R^2$ and $R^3$ are isobutyl group.

In one embodiment, the present invention provides a compound of Formula I, wherein $R^4$ is hydrogen.

In one embodiment, the present invention provides a compound of Formula I, wherein $L_1$, $L_2$, $L_3$ are each independently $C_1$-$C_4$ branched or unbranched alkyl chain.

In one embodiment, the present invention provides a compound of Formula I, wherein $L_1$ is —$(CH_2)_3$—, $L_2$ is —$(CH_2)_3$—, and $L_3$ is —$(CH_2)$—.

In one embodiment, the present invention provides a compound of Formula I, wherein $R^1$ or $R^1$—X represents an antibiotics moiety of an antibiotics, and wherein the antibiotics is selected from the group consisting of Gentamicin, Streptomycin, Kanamycin, Fradiomyctn, Paromomycin, Tobramycin, Netilmicin, Amikacin, Neomycin, Ribostamycin, Dibekacin, Sisomicin, Isepamicin, Bekanamycin, Astromicin, Plazomicin, Vancomycin, Linezolid, Erythromycin, Eperezolid, and any derivative thereof; $R^2$ and $R^3$ are isobutyl group; $R^4$ is hydrogen; $L_1$ is —$(CH_2)_3$—, $L_2$ is —$(CH_2)_3$—, and $L_3$ is —$(CH_2)$—; X is O; and n is 4.

In one embodiment, the present invention provides a compound of Formula I, wherein $R^1$ or $R^1$—X represents an aminoglycoside antibiotics moiety of an antibiotics, and wherein the antibiotics is selected from the group consisting of Gentamicin, Kanamycin, Tobramycin, Amikacin, Neomycin, Plazomicin, and any derivative thereof; $R^2$ and $R^3$ are isobutyl group; $R^4$ is hydrogen; $L_1$ is —$(CH_2)_3$—, $L_2$ is —$(CH_2)_3$—, and $L_3$ is —$(CH_2)$—; X is O; and n is 4.

In one embodiment, the present invention provides a compound of Formula I, wherein $R^1$ or $R^1$—X represents an aminoglycoside antibiotics moiety, and the aminoglycoside antibiotics is Kanamycin or any derivative thereof; $R^2$ and $R^3$ are isobutyl group; $R^4$ is hydrogen; $L_1$ is —$(CH_2)_3$—, $L_2$ is —$(CH_2)_3$—, and $L_3$ is —$(CH_2)$—; X is O; and n is 4.

In one embodiment, the present invention provides a compound of Formula I with the specific structure Formula A, wherein the antibiotic moiety is a Kanamycin moiety:

In one embodiment, the present invention provides a compound of Formula II, wherein $R^1$ represents the moiety of an aminoglycoside antibiotics or any derivative thereof.

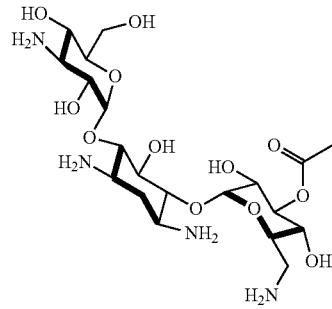
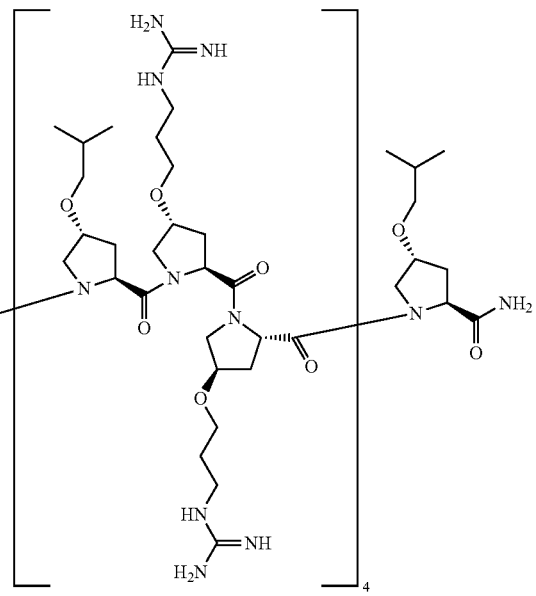

A

In another aspect, the present disclosure provides a compound of Formula II:

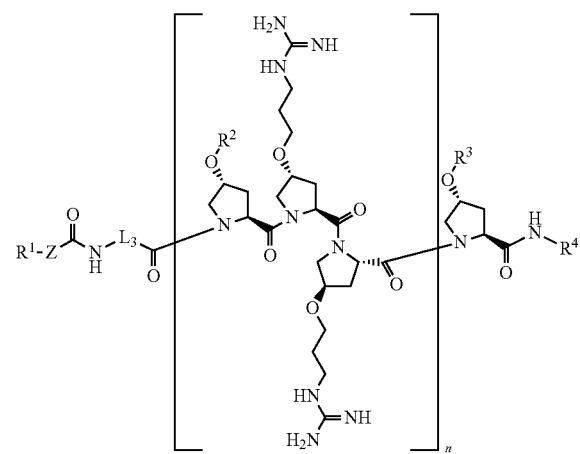

II or a stereoisomer, tautomer, solvate, pharmaceutically acceptable salt, derivative or prodrug thereof, wherein
$R^1$ is an antibiotic moiety;
$R^2$ and $R^3$ are each independently H, a $C_1$-$C_8$ branched or unbranched alkyl chain, or a $C_3$-$C_8$ cyclic alkyl;
$R^4$ is H, a $C_1$-$C_8$ branched or unbranched alkyl chain, or a $C_3$-$C_8$ cyclic alkyl;
$L_3$ is $C_1$-$C_8$ branched or unbranched alkyl chain, or a $C_3$-$C_8$ cyclic alkyl;
Z is a linker comprising a disulfide bond (S—S bond); and
n is 3-8.

In one embodiment, the present invention provides a compound of Formula II, wherein $R^1$ represents an aminoglycoside antibiotics moiety, wherein the aminoglycoside antibiotics is selected from the group consisting of Gentamicin, Streptomycin, Kanamycin, Fradiomyctn, Paromomycin, Tobramycin, Netilmicin, Amikacin, Neomycin, Ribostamycin, Dibekacin, Sisomicin, Isepamicin, Bekanamycin, Astromicin, Plazomicin, and any derivative thereof.

In one embodiment, the present invention provides a compound of Formula II, wherein $R^1$ represents an antibiotics moiety of an antibiotics, wherein the antibiotics is selected from the group consisting of Vancomycin, Linezolid, Erythromycin, Eperezolid, and any derivative thereof.

In one embodiment, the present invention provides a compound of Formula II, wherein $R^1$ represents an antibiotics moiety of an antibiotics, wherein the antibiotics is selected from the group consisting of Gentamicin, Streptomycin, Kanamycin, Fradiomyctn, Paromomycin, Tobramycin, Netilmicin, Amikacin, Neomycin, Ribostamycin, Dibekacin, Sisomicin, Isepamicin, Bekanamycin, Astromicin, Plazomicin, Vancomycin, Linezolid, Erythromycin, Eperezolid, and any derivative thereof In one embodiment, the present invention provides a compound of Formula II, wherein $R^2$ and $R^3$ are each independently $C_1$-$C_4$ branched or unbranched alkyl chain.

In one embodiment, the present invention provides a compound of Formula II, wherein $R^2$ and $R^3$ are isobutyl group.

In one embodiment, the present invention provides a compound of Formula II, wherein $R^4$ is hydrogen.

In one embodiment, the present invention provides a compound of Formula II, wherein $L_3$ is $C_1$-$C_4$ branched or unbranched alkyl chain.

In one embodiment, the present invention provides a compound of Formula II, wherein $L_3$ is —$(CH_2)$—.

In one embodiment, the present invention provides a compound of Formula II, wherein the linker Z is —(C═O)—(CH$_2$)$_3$—S—S—(CH$_2$)$_3$—, and the carbonyl group (C═O) of the linker Z is connected to the antibiotic moiety R$^1$ through an oxygen or nitrogen to form a ester or amide group.

In one embodiment, the present invention provides a compound of Formula II, wherein n is 4.

In one embodiment, the present invention provides a compound of Formula II, wherein R$^1$ represents an aminoglycoside antibiotics moiety of an antibiotics, and wherein the antibiotics is selected from the group consisting of Gentamicin, Streptomycin, Kanamycin, Fradiomyctn, Paromomycin, Tobramycin, Netilmicin, Amikacin, Neomycin, Ribostamycin, Dibekacin, Sisomicin, Isepamicin, Bekanamycin, Astromicin, Plazomicin, and any derivative thereof; R$^2$ and R$^3$ are isobutyl group; R$^4$ is hydrogen; L$_3$ is —(CH$_2$)—; Z is —(C═O)—(CH$_2$)$_3$—S—S—(CH$_2$)$_3$—, and the carbonyl group (C═O) of the linker Z is connected to the antibiotic moiety R$^1$ through an oxygen or nitrogen to form a ester or amide group; and n is 4.

In one embodiment, the present invention provides a compound of Formula II, wherein R$^1$ represents an antibiotics moiety of an antibiotics, and wherein the antibiotics is selected from the group consisting of Vancomycin, Linezolid, Erythromycin, Eperezolid, and any derivative thereof; R$^2$ and R$^3$ are isobutyl group; R$^4$ is hydrogen; L$_3$ is —(CH$_2$)—; Z is —(C═O)—(CH$_2$)$_3$—S—S—(CH$_2$)$_3$—, and the carbonyl group (C═O) of the linker Z is connected to the antibiotic moiety R$^1$ through an oxygen or nitrogen to form a ester or amide group; and n is 4.

In one embodiment, the present invention provides a compound of Formula II, wherein R$^1$ represents an antibiotics moiety of an antibiotics, wherein the antibiotics is selected from the group consisting of Gentamicin, Kanamycin, Tobramycin, Amikacin, Neomycin, Plazomicin, and any derivative thereof; R$^2$ and R$^3$ are isobutyl group; R$^4$ is hydrogen; L$_3$ is —(CH$_2$)—; Z is —(C═O)—(CH$_2$)$_3$—S—S—(CH$_2$)$_3$—, and the carbonyl group (C═O) of the linker Z is connected to the antibiotic moiety R$^1$ through an oxygen or nitrogen to form a ester or amide group; and n is 4.

In one embodiment, the present invention provides a compound of Formula II, wherein the linker Z is —X—(C═O)-L$_1$-S—S-L$_2$-, wherein L$_1$ and L$_2$ are each independently C$_1$-C$_8$ branched or unbranched alkyl chain, or a C$_3$-C$_8$ cyclic alkyl; X is O or NR$^5$, wherein R$^5$ is H, C$_1$-C$_8$ branched or unbranched alkyl chain, or a C$_3$-C$_8$ cyclic alkyl, or X combined with R$^1$ together is an antibiotic moiety.

In one embodiment, the present invention provides a compound of Formula I or II, wherein R$^1$ or R$^1$—X represents Tobramycin moiety or any derivative thereof.

In one embodiment, the present invention provides a compound of Formula I or II, wherein the compound is:

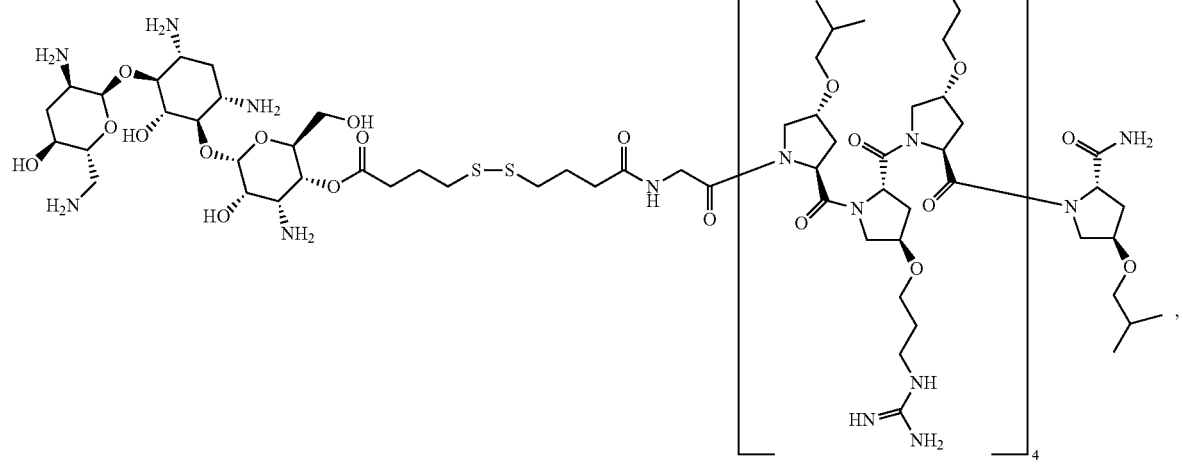

or a stereoisomer, tautomer, solvate, pharmaceutically acceptable salt, derivative or prodrug thereof.

The present disclosure also provides methods for treating a host cell having a microbial infection comprising the steps of administering a compound of Formula I or Formula II, or a stereoisomer, tautomer, solvate, pharmaceutically acceptable salt, derivative or prodrug thereof.

The present disclosure further provides methods for treating a patient, either mammal or animal, having a microbial infection with a compound of Formula I or Formula II, or a stereoisomer, tautomer, solvate, pharmaceutically acceptable salt, derivative or prodrug thereof.

The present disclosure provides methods for inhibiting formation of a biofilm by a compound of Formula I or Formula II, or a stereoisomer, tautomer, solvate, pharmaceutically acceptable salt, derivative or prodrug thereof.

The present disclosure provides methods for inhibiting growth of an established biofilm with a compound of Formula I or Formula II, or a stereoisomer, tautomer, solvate, pharmaceutically acceptable salt, derivative or prodrug thereof. In one aspect, the compound used for any method is:

The compounds of the present invention may be prepared by a variety of procedures, some of which are illustrated in the schemes below. Some substituents may be eliminated in the following schemes for the sake of clarity and are not intended to limit the teaching of the schemes in any way.

The method of preparing Examples 1-3 is illustrated in Scheme 1. A person with ordinary skill in the art may appreciate that the method to prepare Examples 1-3, may

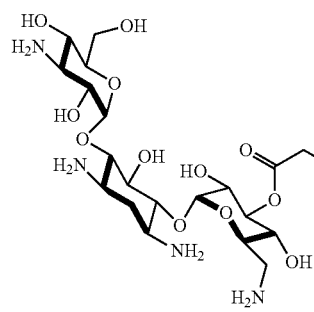
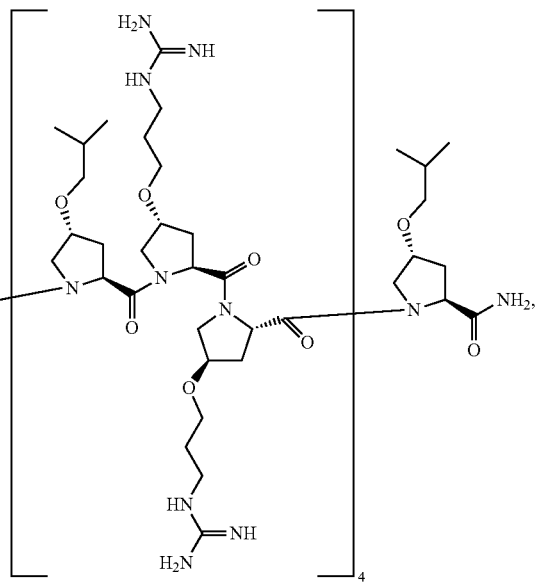
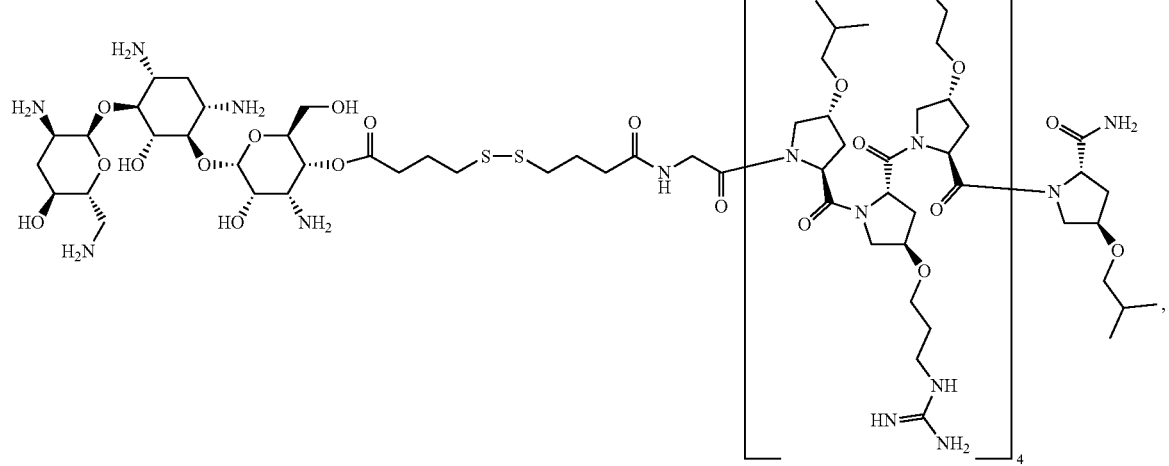

or a stereoisomer, tautomer, solvate, pharmaceutically acceptable salt, derivative or prodrug thereof.

apply to the method of preparing other compounds disclosed in the present invention without undue experiment.

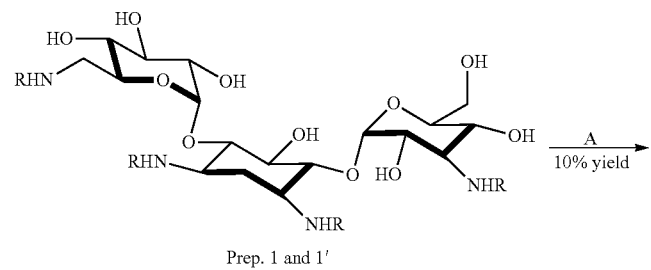
Prep. 1 and 1'
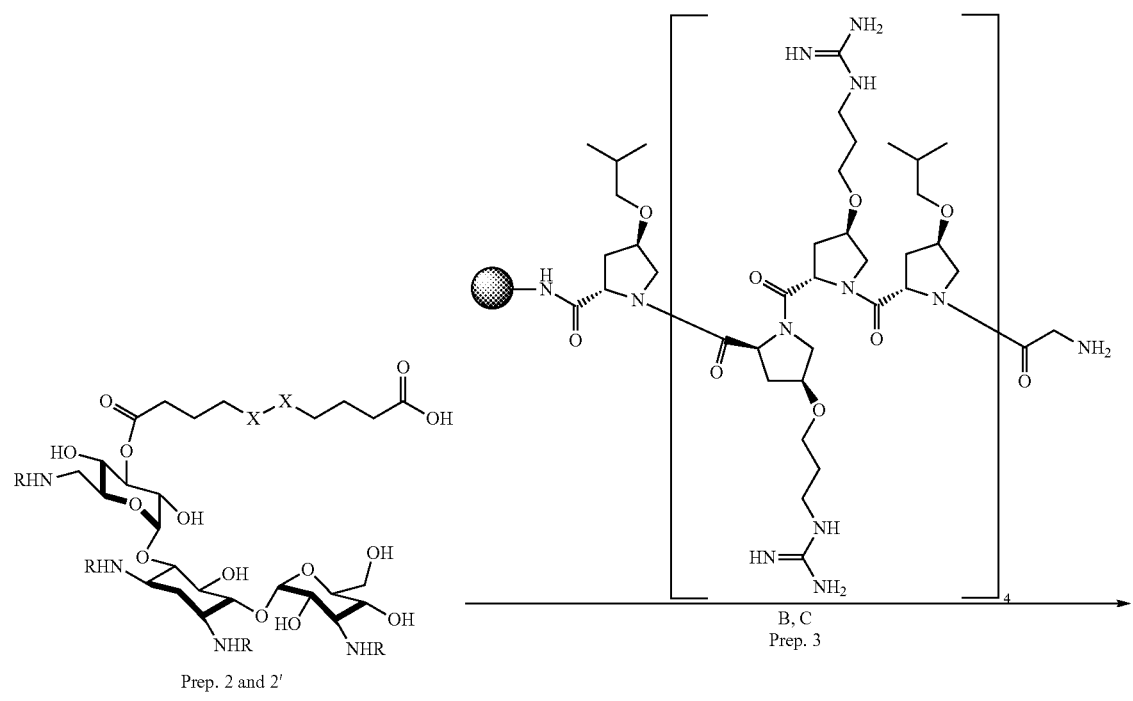
Prep. 2 and 2'

Prep.1 (R=Boc) Prep.1' (R=Cbz)
Prep.2 (R=Boc; X=S); Prep.2' (R=Cbz; X=S); Prep 2" (R=Boc; X=C)
Prep.3 (P14LRR on resin)

Society, 2005, 127, 11798-803. Geisler, I.; Chmielewski, J., Probing length effects and mechanism of cell penetrating agents mounted on a polyproline helix scaffold. *Bioorg. Med. Chem. Lett.,* 2007, 17, 2765-8.

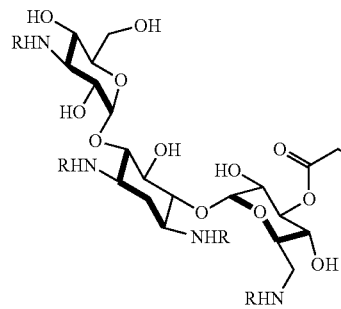
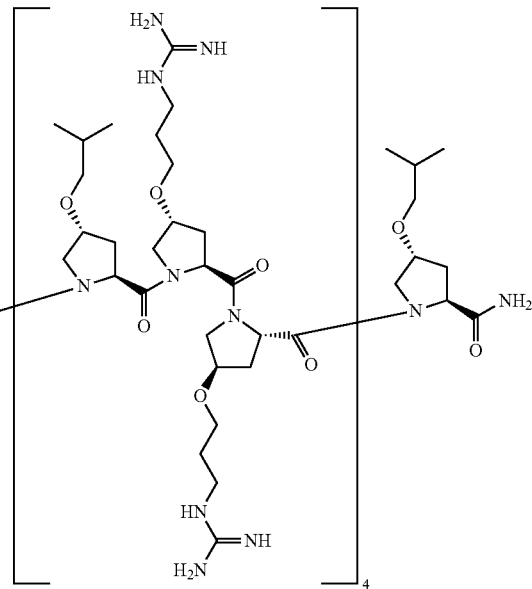

Example 1 (R=H; X=S); Example 2 (R=H, X=C); Example 3 (R=Cbz, X=S)

Scheme 1: The Method of Preparing Compounds of Formula A

Preparation 1 or 1', which is a Kanamycin analog with amino groups protected by an appropriate nitrogen-protecting group such as a tert-butyloxycarbonyl (Boc) group or carboxybenzyl (Cbz), can be prepared by methods disclosed in literatures. See Disney, M. D.; Barrett, O. J. *Biochemistry (Mosc.)* 2007, 46 (40), 11223; and Chen, G.; Pan, P.; Yao, Y.; Chen, Y.; Meng, X.; Li, Z. *Tetrahedron* 2008, 64 (38), 9078.

For example, Preparations 1 can react with an appropriate acid such as 4,4'-dithiodibutyric acid in Step A under an appropriate reaction conditions to provide Preparation 2. Preparation 2 may further react with Preparation 3 (resin-bound P14LRR) in Step B, followed by the treatment of trifluoroacetic acid in Step C to provide Example 1.

The resin-bound P14LRR was synthesized using Fmoc-based, solid phase strategy on the Rink amide ChemMatrix resin, as previously described. See Fillon, Y. A.; Anderson, J. P.; Chmielewski, J., Cell penetrating agents based on a polyproline helix scaffold *Journal of the American Chemical*

Preparations

Preparation 1: di-tert-butyl ((1S,3R,4S,5R,6R)-4-(((2S,3R,4S,5S,6R)-4-((tert-butoxycarbonyl)amino)-3,5-dihydroxy-6-(hydroxymethyl)tetrahydro-2H-pyran-2-yl)oxy)-6-(((2R,3R,4S,5S,6R)-6-(((tert-butoxycarbonyl)amino)methyl)-3,4,5-trihydroxytetrahydro-2H-pyran-2-yl)oxy)-5-hydroxycyclohexane-1,3-diyl)dicarbamate (Tetra-N-(tert-butoxycarbonyl) kanamycin A)

Tetra-N-(tert-butoxycarbonyl) kanamycin A (Preparation 1 is prepared with method disclosed in Disney, M. D.; Barrett, O. J. *Biochemistry (Mosc.)* 2007, 46 (40), 11223.)

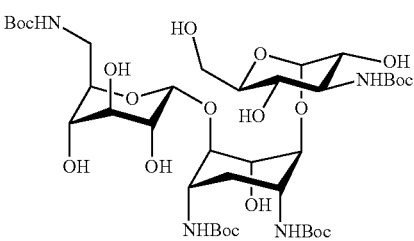

Preparation 1'

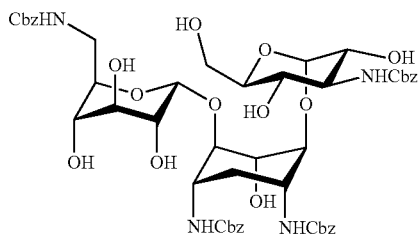

Preparation 1' was prepared with essentially the same method of Preparation 1 except the protecting group is carboxybenzyl group (Cbz).

Preparation 2: 4-((4-(((2R,3R,4S,5R,6R)-2-(((1R,2R,3S,4R,6S)-4,6-bis((tert-butoxycarbonyl)amino)-3-(((2S,3R,4S,5S,6R)-4-((tert-butoxycarbonyl)amino)-3,5-dihydroxy-6-(hydroxymethyl)tetrahydro-2H-pyran-2-yl)oxy)-2-hydroxycylohexyl)oxy)-6-((((tert-butoxycarbonyl)amino)methyl)-3,5-dihydroxytetrahydro-2H-pyran-4-yl)oxy)-4-oxobutyl)disulfanyl)butanoic acid

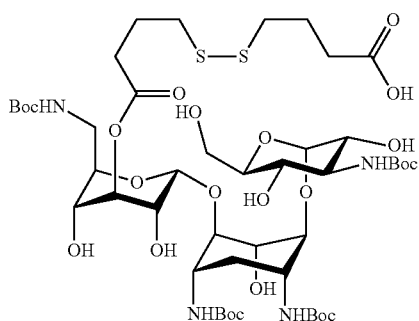

To a solution of 4,4'-dithiodibutyric acid (5.9 mmol) in 5 mL of dry dimethylformamide (DMF), at room temperature, was added O-(7-azabenzotriazole-1-yl)-N,N,N,N'-tetramethyluronium hexafluorophosphate (HATU) (5.2 mmol) and diisopropylethylamine (DIEA) (27 mmol). After 20 min at RT, Preparation 1 (2.3 mmol) was added. The mixture was stirred overnight. The solvent was removed in vacuo, and the resulting material was dissolved in dimethylsulfoxide (DMSO) and purified by reversed phase HPLC using a C8 and C18 semi-preparative column (Phenomenix). An eluent consisting of solvent A (acetonitrile and 0.1% trifluoroacetic acid (TFA)) and solvent B (water and 0.1% TFA) with a 60 min gradient of 35-95% solvent A, a flow rate of 10 mL/min and ELS detection were used for Preparation 2. Fractions consisting of the desired products were collected and lyophilized to obtain Preparation 2 (approximately a 10% yield). The structure was elucidated using 2D NMR methods COSY, TOCSY and HMBC.

Preparation 2'

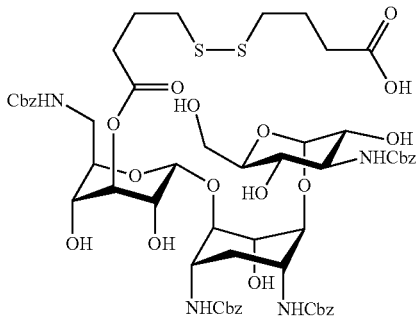

Preparation 2' was prepared with essentially the same method of Preparation 2 except the protecting group is carboxybenzyl group (Cbz).

Preparation 2"

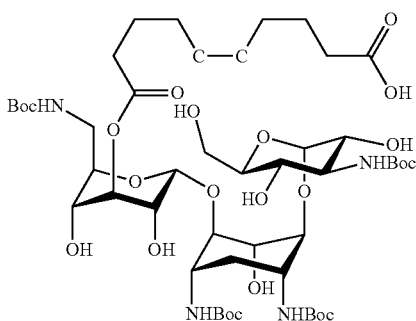

Preparation 2" was prepared with essentially the same method of Preparation 2 except that X is C.

Preparation 3: Resin Bound P14LRR

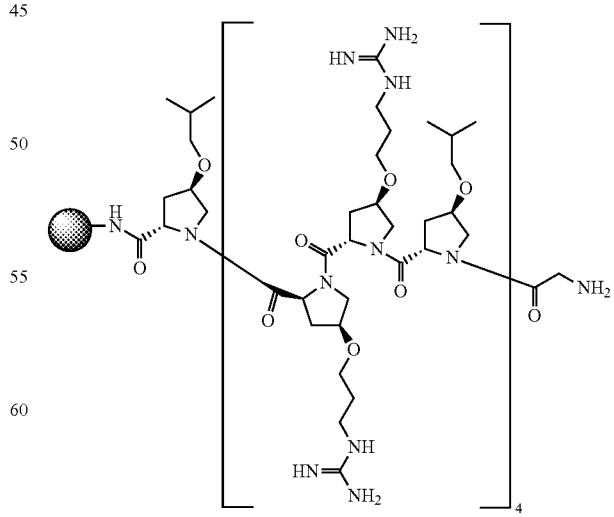

Preparation 3 was synthesized using Fmoc-based, solid phase strategy on the Rink amide ChemMatrix resin (45 tmol), as previously described methods. The procedure was repeated until all amino acids were coupled to the resin. The resin was washed with dimethylformamide (DMF), dichloromethane (DCM), methanol (MeOH), DCM and DMF (2×5 mL). See Fillon, Y. A.; Anderson, J. P.; Chmielewski, J., Cell penetrating agents based on a polyproline helix scaffold. *Journal of the American Chemical Society,* 2005, 127, 11798-803. Geisler, I.; Chmielewski, J., Probing length effects and mechanism of cell penetrating agents mounted on a polyproline helix scaffold. *Bioorg. Med. Chem. Lett.,* 2007, 17, 2765-8.

Example 1

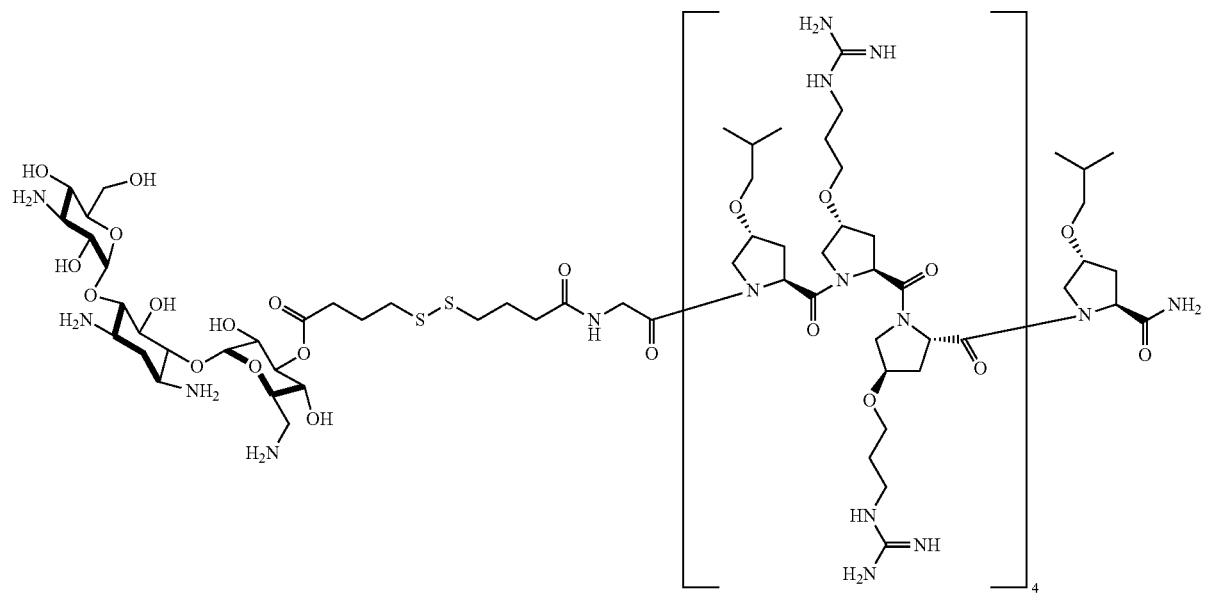

Preparation 2 (2 equiv., 0.12 mmol) in DMF (5 mL), HATU (2 equiv., 0.12 mmol) and diisopropylethylamine (DIEA) (4 equiv., 0.24 mmol) were added to the resin Preparation 3 and the reaction flask was agitated for 24 h. The resin was washed with DMF, DCM, MeOH, and DCM (2×5 mL). A trifluoroacetic acid (TFA) cleavage cocktail TFA:triisopropylsilane:water (95:2.5:2.5) (10 mL) was added to the resin and the mixture was agitated for 1 h. The solution was filtered through glass wool into a 50 mL centrifuge tube. The resin was washed with DCM (4×4 mL), and the filtrate was collected into the same tube. The resulting solution was concentrated in vacuo to remove the TFA. The residue wa sdissolved in cold diethyl ether and placed in the freezer to precipitate the desired peptide conjugates. The precipitate was collected by centrifugation and washed with cold diethyl ether. The collected materials was purified to homogeneity by reversed phase HPLC using $C_{18}$ semi-preparative column (Phenomenix). An eluent consisting of solvent A (acetonitrile and 0.1% TFA) and solvent B (water and 0.1% TFA) with a flow rate of 12 mL/min, UV detection at 214 nm and 60 min solvent gradient of 15-60% for Example 1. Expected Mass 3302.87, Observed Mass 3303.46.

Examples 2-4 were prepared with essentially the same method of Example 1.

TABLE 1
Examples 2-4
Example 2
R = H, X = C
Expected Mass 3266.96,
Observed Mass 3268.59
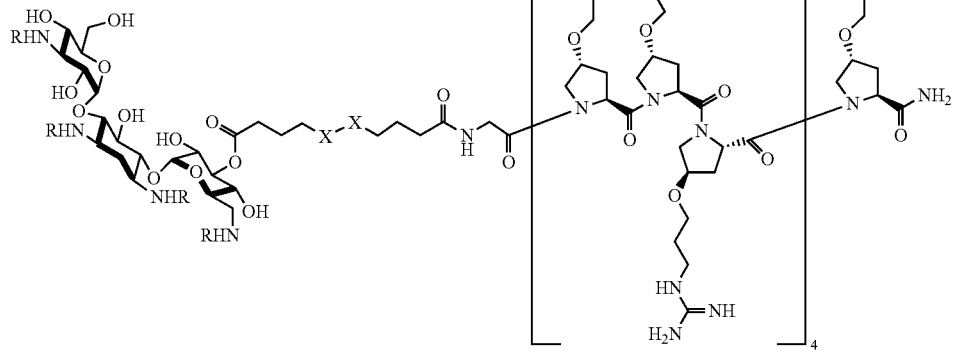
Example 3
R = Cbz, X = S
Expected Mass 3839.02,
Observed Mass 3844.22
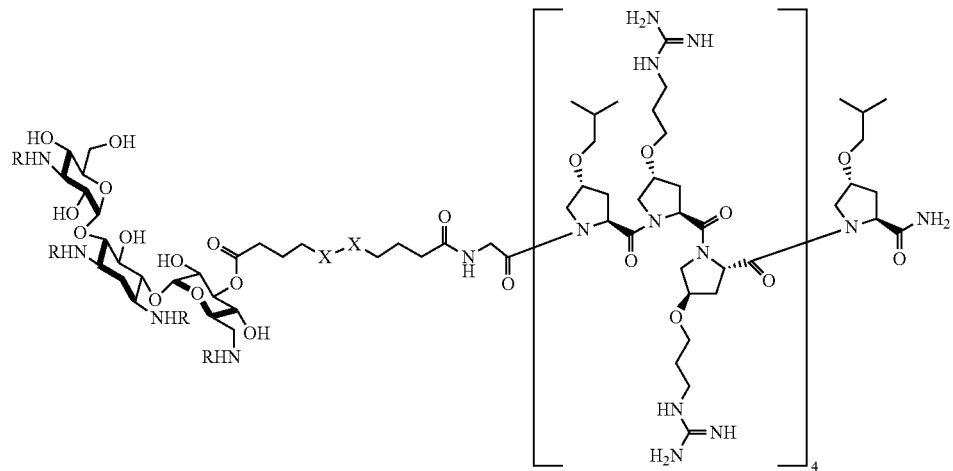
Example 4
Expected Mass 3814.5,
Observed Mass 3810.17
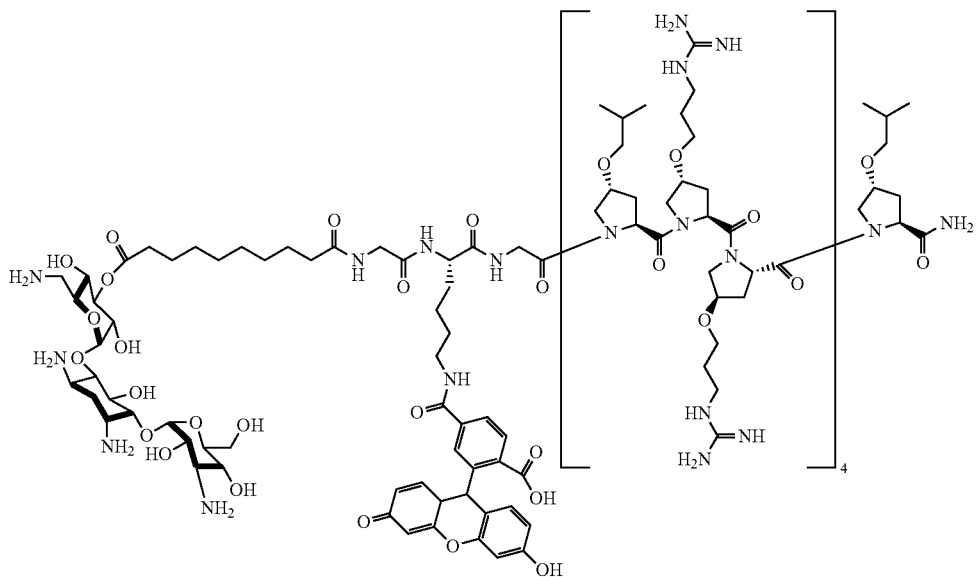

Example 5

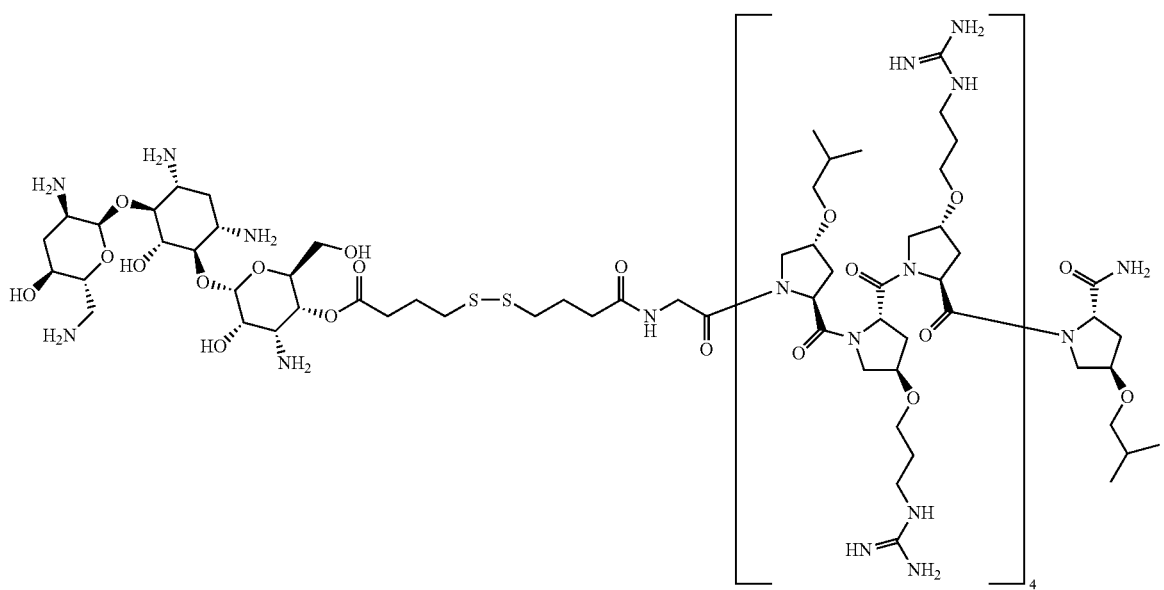

Example 5 was synthesized with the method illustrated in Scheme 2.

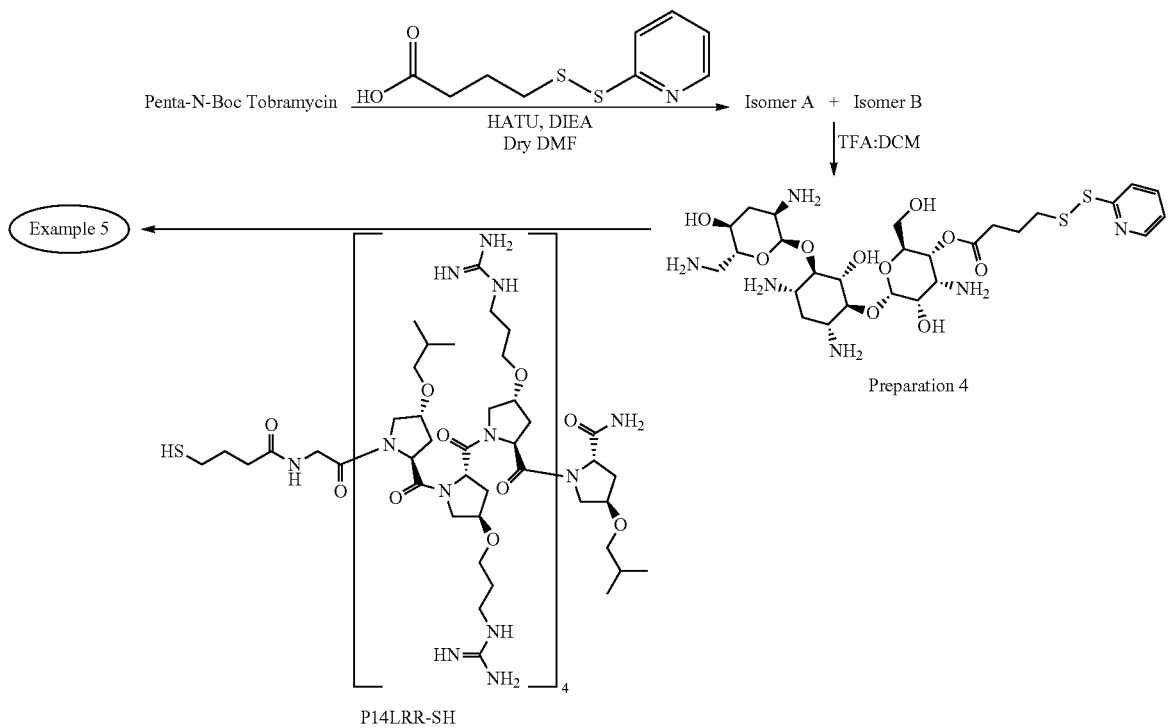

Preparation 4

To a flame dried flask equipped with stir bar, Penta-N-Boc Tobramycin (CAS No.: 172950-21-9; 101.3 mg, 0.105 mmol), 4-(2-pyridyldithio)butanoic acid (20 mg, 0.087 mmol), diisopropylethylamine (DIEA) (182 μL, 1.05 mmol), HATU (24.5 mg, 0.105 mmol) were added with 4 Å molecular sieves in 500 μL dry N, N' dimethylformamide (DMF). The reaction was stirred for 72 hours and reverse phase HPLC was used to determine reaction completeness. The reaction components were purified to homogeneity via reverse phase HPLC (C18, 55-75% CH$_3$CN in water with 0.1% TFA, 254 nm), to afford 2 major esterification isomers, "A" and "B", as white powders with yields of 7.9 mg (6.4%) and 17 mg (13.8%), respectively. MS (ESI) m/z: calculated [M+H]: 1179.5, Observed: 1179.6.

Isomer A (5.9 mg, 0.005 mmol), was placed in a vial equipped with stir bar, and 139 µL each of dichloromethane (DCM) and trifluoroacetic acid (TFA) were added. The reaction was monitored by TLC (30% methanol:70% dichloromethane) and was judged complete after 1.5 hour. The reaction mixture was concentrated under reduced pressure. Reaction mixture was resuspended in methanol (250 µL, 2×) and dichloromethane (250 µL, 2×) and the solvents removed under reduced pressure to yield a white solid. The formation of the desired material was confirmed by mass spectrometry, and used in the next step without further purification. Yield: 6.5 mg (79.3%). MS (ESI) m/z: calculated [M+H]: 679.3, Observed: 679.3. Structure of Preparation 4 was confirmed by 1D- and 2D-NMR techniques, including $H^1$, $C^{13}$, DEPT-135, COSYPR, TOCSYPR, HMBC and HSQC.

Example 5

To an Eppendorf tube containing the P14LRR-SH peptide (1 mg, 0.3 µmol) in degassed water (186 µL, pH 9) was added dropwise Preparation 4 (2.3 mg, 3 µmol) in degassed water (117 µL, pH 9). The reaction was allowed to react overnight, and the reaction progress was monitored with reverse phase HPLC. The desired conjugate Example 5 was purified to homogeneity via reverse phase HPLC (C18, 20-80% $CH_3CN$ in water with 0.1% TFA, 214 nm). The product fractions were combined, acetonitrile was removed under reduced pressure and the resulting aqueous solution was lyophilized to afford an off white solid Example 5. Yield: 0.2 mg (20%). MS (MALDI) m/z: calculated: 3285.9, observed: 3285.3.

Characterization of the Conjugates—Analytical HPLC

Purity was determined by analytical RP-HPLC using a C18 reverse phase analytical column (5 µm, 4 mm× 250 mm; Phenomenex Luna), a flow rate of 1.2 mL/min, UV detection at 214 nm, and a 30 mingradient of 15-55%, 25-55% and 30-70% solvent A (A: acetonitrile and 0.05% trifluoroacetic acid (TFA) gradient of 15-55%, 25-55% and 30-70% solvent A (A: acetonitrile and 0.05% trifluoroacetic acid (TFA); B: water and 0.05% TFA).

The dual antibiotic conjugate Example 1 was designed to enter mammalian cells and release kanamycin and the peptide within an intracellular reducing environment. To evaluate the half-life of release of these agents under reducing conditions, Example 3 was constructed as it will release the UV-active fragment. The conjugate Example 3 (100 µM in a 1:1 mixture of PBS buffer and DMF) was treated with 1 mM dithiothreitol (DTT) and the accumulation of kanamycin fragment was monitored by HPLC and LC-MS. Efficient release from the conjugate with a half-life of 1.5±0.2 h and full release after 4 h was observed.

Characterization of the Conjugates—Mass Spectrometry

Peptides were further characterized using matrix associated laser desorption ionization-time of flight (MALDI-TOF) mass spectrometry (Voyager DE, Applied Biosystems).

Method for Example 1 Stability Studies Using Porcine Liver Esterase

To a solution of PBS, pH 7.4 (690 µL PBS) was added, 10 µL of 10 mM Example 1 (to give a final concentration of 100 µM) and 300 µL of porcine liver esterase in PBS, pH 7.4 (to give a final concentration of 100 unit/ml). The mixture was incubated at 37° C. At different time points, 50 µL aliquots from the reaction mixture was removed and 50 µL of cold acetonitrile was added to deactivate the proteins. The solution was then vortexed for 20 sec and centrifuged for 10 min at 2000 rpm. Next, 50 µL of the supernatant was removed, added to 50 µL of 100 mM N-α-Benzoyl-L-arginine ethyl ester hydrochloride (BAEE) (Alfa Aesar A18181) (to give final concentration 500 µM) as an internal standard, and was immediately injected on an HPLC equipped with a $C_{18}$ reverse phase analytical column (5 µm, 4 mm×250 mm; Phenomenex Luna) with an eluent consisting of solvent A (acetonitrile and 0.1% trifluoroacetic acid (TFA)) and solvent B (water and 0.1% TFA) with a 30 min gradient of 15-65% solvent A, a flow rate of 1.2 mL/min and UV detection at 214 nm. The appearance of the peak corresponding to P14LRR modified with 4,4'-dithiodibutyric acid was monitored and only ~15% release was observed after 120 hrs. Therefore, Example 1 is not susceptible to esterase cleavage likely due to steric crowding on kanamycin around the ester bond.

Method for In Vitro Antimicrobial Activity Assessment
a) Against *Escherichia coli* and *Staphylococcus aureus*

*Escherichia coli* (ATCC 25922) or *Staphylococcus aureus* (ATCC 25923) was grown to the mid-exponential phase in Tryptic Soy Broth (TSB) at 37° C. with shaking. An aliquot of the bacterial suspension was centrifuged for 5 min at 3000 rpm, the supernatant aspirated and the pellet re-suspended in Muller Hinton Broth (MHB) to a final optical density of 0.001 as measured by absorbance at 600 nm ($OD_{600}$). Next 90 µL of this culture was added in a sterile 96-well plate (Cellstar 655180) and then supplemented with 10 µL of sterile water or two-fold serial dilutions of the drugs in water. Melittin was used as positive control for both bacterial strains. The plate was then incubated for 6 h at 37° C. The $OD_{590}$ was determined using a microplate reader (TECAN SpectraFluor Plus). The minimum inhibitory concentration (MIC) was defined as the lowest concentration of drug at which no growth was observed. Data was obtained in duplicates from at least two independent experiments.

Against Pathogenic Bacteria

The broth microdilution technique was used to determine the minimum inhibitory concentrations (MIC) of drugs according to the guidelines of the Clinical and Laboratory Standards Institute (CLSI). *Salmonella enteritidis*, *Shigella flexneri*, *Brucella abortus*, or *Mycobacterium smegmatis* were diluted to a bacterial inoculum of $5\times10^5$ colony forming unit (CFU/mL) in Mueller-Hinton broth (MHB) (*S. enteritidis*, and *S. flexneri*), Brain Heart Infusion broth (BHI) (*B. abortus*), and Tryptic Soy Broth (TSB) (*M. smegmatis*). Drugs were added to polystyrene 96 well plates (CytoOne, CC7672-7596) at desired concentrations and plates were incubated at 37° C. for 18 h (*S. flexneri*), 24 h (*S. enteritidis*) or 48 h (*B. abortus* and *M. smegmatis*). MIC was defined as the lowest concentration of drug which inhibited the visible growth of bacteria.

The resazurin microtiter assay (REMA) was used to determine the minimum inhibitory concentrations (MIC) of drugs against *Mycobacterium tuberculosis* H37Ra. Briefly, 100 µL of Middlebrook 7H9 broth supplemented with Oleic Albumin Dextrose Catalase Growth Supplement (OADC) enrichment and glycerol was added to wells of 96-well plate, and serial two fold dilutions of each drug were prepared directly in the plate. One hundred microliters of inoculum was added to each well. A growth control and a sterile control were also included for each isolate. The plate was covered, sealed in a plastic bag, and incubated at 37° C. under a normal atmosphere. After 7 days of incubation, 30 µL of resazurin solution was added to each well, and the plate was reincubated for 24 hr. A change in color from blue to pink indicated bacterial growth, and the MIC was determined as the minimum concentration of drug that prevented color change.

c) Determination of Minimum Inhibitory Concentration (MIC) Values Against Biofilmforming Clinical Isolates of *S. aureus* and *S. epidermidis*

Biofilm-forming clinical isolates of *S. aureus* (ATCC 6538) and *S. epidermidis* (ATCC 35984) were grown overnight in TSB. After incubation, cultures were diluted to $5 \times 10^5$ colony forming unit (CFU/ml) in MHB. The minimum inhibitory concentrations of compounds were determined via the broth microdilution technique according to the guidelines of the Clinical and Laboratory Standards Institute (CLSI). Compounds were added to polystyrene 96-well plates at desired concentrations and subsequently serially diluted. The MIC was defined as the lowest concentration of peptide or antibiotic that inhibited bacterial growth visually.

represents a 2-4 fold improvement in the MIC relative to kanamycin against kanamycin-sensitive strains and 128 to >256-fold improvement in the MIC relative to kanamycin against kanamycin-resistant strains. Interestingly, Example 1 demonstrated potent activity against several multidrug-resistant clinical isolates including methicillin-resistant *S. aureus* (MRSA USA400), methicillin-resistant *S. epidermidis* (MRSE) and vancomycin-resistant *E. faecium* (VRE) (Table 1). Of particular note, Example 1 demonstrated potent activity against *A. baumannii* ATCC BAA-1605, a multidrug-resistant isolate obtained from the sputum of a Canadian soldier serving in Afghanistan. This strain is resistant to numerous antibiotics including kanamycin, meropenem, imipenem, ceftazidime, ciprofloxacin, piperacillin, ticarcillin, cefepime, aztreonam and gentamicin (Table 1). Moreover, Example 1 demonstrated potent activity against colistin-resistant *P. aeruginosa* (1109) isolated from a cystic fibrosis patient. This isolate exhibits high-level

TABLE 2

MIC values [µM] for the antibacterial activity of the dual conjugates compared to individual component.

| | *E. coli* | *S. aureus* | *S. enteritidis* | *B. abortus* | *S. flexneri* | *M. smegmatis* | *M. tuberculosis* | *S. aureus*[c] | *S. epidermis*[c] |
|---|---|---|---|---|---|---|---|---|---|
| P14LRR | 4 | 16 | 32 | 16 | 8 | 8 | 16 | 16 | 8 |
| P14SH | 4 | 16 | 4 | 2 | 4 | 4 | 8 | — | — |
| kanamycin | 2 | 2 | 16 | 4 | 2 | 8 | 2 | 4 | >128 |
| P14LRR:kanamycin[b] | 2 | 2 | 8 | 4 | 2 | 4 | 1 | — | — |
| Example 1 | 2 | 2 | 2 | 0.12 | 1 | 1 | 1 | 1 | 1 |
| Example 2 | 2 | 16 | 8 | 2 | 2 | 2 | 1 | — | — |

[a]The minimum inhibitory concentration,
[b]1:1 mixture of P14LRR and kanamycin
[c]clinical isolate that forms biofilms Antimicrobial Activity The antibacterial activity of kanamycin and the conjugate was investigated against ESKAPE pathogens. The peptide, P14LRR, alone displayed moderate to weak antibacterial activity against ESKAPE pathogens with MIC values ranging from 8 to 64 µM (Table 1). Kanamycin was only active against two strains (*S. aureus* ATCC 6538 and MRSA USA400). However, other bacteria were resistant to kanamycin (MIC, 128 to >256 µM). Example 1 demonstrated a very potent, broad-spectrum antibacterial activity over kanamycin and the peptide (P14LRR). The MIC of Example 1 was 1 to 2 µM against all strains tested. This resistance to colistin (MIC=128 µM), kanamycin and several antimicrobial peptides. Colistin is an antibiotic of last resort for multidrug-resistant *P. aeruginosa* infections. The emergence of resistant isolates to colistin, particularly via plasmid-mediated resistance in Enterobacteriaceae, highlights the urgent need to discover new antimicrobial agents to address this issue. The discovery that Example 1 has potent activity against a colistin-resistant *P. aeruginosa* strain indicates a potential therapeutic advantage of P14KanS over several antimicrobials that are ineffective against colistin-resistant *P. aeruginosa*.

TABLE 3

Minimum inhibitory concentration (MIC) (µM) of compounds against clinical and drug-resistant bacterial isolates

| Compound | Methicillin-resistant *S. aureus* USA400 | *S. aureus* ATCC 6538 | *S. epidermidis* ATCC 35984 | *P. aeruginosa* ATCC PAO1 | Colistin-resistant *P. aeruginosa* 1109 | *A. baumannii* BAA-1605 | *K. pneumoniae* BAA-1706 | Vancomycin-resistant *E. faecium* ATCC 700221 |
|---|---|---|---|---|---|---|---|---|
| Phenotype | Resistant to methicillin and tetracycline | Biofilm forming strain, methicillin sensitive | Prototype biofilm producer, resistant to methicillin, gentamicin, kanamycin, erythromycin, clindamycin and trimethoprim | Biofilm producing strain. Resistant to kanamycin | Isolated from a cystic fibrosis patient. Resistant to colistin and kanamycin | A multidrug-resistant strain; resistant to kanamycin, ceftazidime, gentamicin, ticarcillin, piperacillin, aztreonam, cefepime, ciprofloxacin, imipenem, | Resistant to kanamycin | Resistant to vancomycin, teicoplanin and kanamycin |

TABLE 3-continued

Minimum inhibitory concentration (MIC) (μM) of compounds against clinical and drug-resistant bacterial isolates

| Compound | Methicillin-resistant S. aureus USA400 | S. aureus ATCC 6538 | S. epidermidis ATCC 35984 | P. aeruginosa ATCC PAO1 | Colistin-resistant P. aeruginosa 1109 | A. baumannii BAA-1605 | K. pneumoniae BAA-1706 | Vancomycin-resistant E. faecium ATCC 700221 |
|---|---|---|---|---|---|---|---|---|
| | | | | | and meropemem | | | |
| P14LRR | 64 | 16 | 32 | 64 | 64 | 32 | 32 | 8 |
| Kanamycin | 4 | 2 | >256 | >256 | >256 | 128 | 256 | >256 |
| Example 1 | 1 | 1 | 1 | 2 | 2 | 1 | 2 | 2 |
| Fold enhancement in MIC compared to kanamycin | 4 | 2 | >256 | >128 | >128 | 128 | 128 | >128 |

Antimicrobial activities of the Example 1 and Example 2 conjugates were evaluated with a series of Gram positive and negative bacteria, including a range of intracellular-pathogens (Table 1). This activity was compared to that obtained for P14LRR, P14SH, kanamycin and a 1:1 mixture of kanamycin and P14LRR. Across the series of bacteria P14KanS is highly active with MIC values ranging from 0.12 to 2 μM, including M. tuberculosis. With four strains of bacteria P14KanS is 2- to 32-times more active, respectively, than the non-covalent mixture of P14LRR and kanamycin. With the exception of E. coli and M. tuberculosis, this conjugate is also 2- to 16-fold more potent than the non-reducible P14KanC conjugate. The activity of P14KanS was also evaluated on clinical isolates of S. aureus and S. epidermis that form biofilms, and the conjugate was 8- to 16-fold more potent than the P14LRR peptide, respectively. It was aslo investigated if the Example 1 and Example 2 conjugates disrupted bacteria membranes by monitoring beta-galactosidase release from E. coli upon addition of the conjugates. At five times their MIC values, no significant release of beta-galactosidase was observed, whereas melittin at 5 times its MIC displayed a substantial level of release as has previously been shown. These data demonstrate that the kanamycin-peptide conjugates do not lyse membranes as the mechanism for their antibacterial activity, as was observed for P14LRR.

These data illustrate that neither kanamycin nor P14LRR is capable of effectively clearing intracellular bacteria on their own, even when co-administered. Only Example 1 conjugate potently clears intracellular pathogens by taking advantage of the non-membrane lytic, mammalian cell penetrating activity of P14LRR to co-deliver kanamycin. When comparing the antimicrobial activity of Example 1 against Salmonella and Brucella, Example 1 is 16-fold more potent against Brucella in vitro (Table 1), but the activity trends switches in cyto with a more effective clearance of Salmonella intracellularly. Both of these pathogens enter macrophages via vacuoles, but ultimately reside in sub-cellular locations such as endosomes and the endoplasmic reticulum, respectively. Since Example 1 localizes to endosomes, it is reasonable that this agent is more effective against Salmonella within mammalian cells. The notable difference in potency between Example 1 and Example 1 demonstrates that it is crucial for the two antibiotics to separate and go their own way within macrophages for optimal performance.

Method for Cytotoxicity Assessment

Cellular toxicity was assessed using the 3-(4,5-dimethyl-thiazol-2-yl)-2,5-diphenyltetrazolium bromide (MTT) cell viability assay. Briefly, $1.5 \times 10^4$ J774A.1 cells suspended in 200 μL, of Dulbecco's Modified Eagle Medium (DMEM) supplemented with 10% heat inactivated Fetal Bovine Serum (FBS), 1% Lglutamine and 1% penicillin/streptomycin were seeded in 96-well plates and incubated at 37° C. in a 5% CO2 atmosphere. The cells were cultured for 24 h (60% confluency) before the assays. At the end of the pre-incubation period, the media was discarded and the cells were washed twice with 100 μL PBS. The J774A.1 cells were further incubated with 100 μL of dilutions ranging from 2.5-30 μM of drugs in DMEM for 9 h. Following incubation, 20 μL of 5 mg/mL MTT (Sigma M5655) in PBS was added per well and the plate was returned to the incubator for an additional 1.5 h. Next, the MTT solution was aspirated and 100 μL of dimethyl sulfoxide (DMSO) per well was added to dissolve formazan crystals formed. For each experiment, a negative control of untreated cells was also analyzed. All samples were run in duplicate, and each experiment was duplicated. The intensity of color was quantified at 590 nm using a 96-well ELISA plate reader (SoftMax ProInc., USA). Results were expressed as the percentage mean absorbance of treated cells in respect to incubation with control. The conjugates and the components display limited cytotoxicity to J774A.1 cells across a range of concentrations.

Method for Rescue of J774A.1 Cells Infected with Pathogenic Bacteria

Macrophage-like cell line (J774A.1) was seeded at a density of $1.5 \times 10^4$ per well in a tissue culture 96-well plate (CytoOne, CC7682-7596) in Dulbecco's Modified Eagle Medium (DMEM) media supplemented with 10% Fetal Bovine Serum (FBS), and incubated at 37° C. in a 5% $CO_2$ atmosphere for 24 h (to 95% confluence). Following incubation, the cells were washed once with DMEM media. Then the cells were infected with Salmonella enteritidis, Shigella flexneri or Brucella abortus (at multiplicity of infection 1:10 for S. enteritidis, and 1:100 for S. flexneri or B. abortus) in DMEM and 10% FBS for 1 h. While for Mycobacterium tuberculosis cells were infected (at multiplicity of infection 1:20) in DMEM and 10% FBS for 4 hr, and for Mycobacterium smegmatis cells were infected (at multiplicity of infection 1:50) in DMEM and 10% FBS for 1 h. After infection the wells were washed three times with 200 μL media with gentamicin (final concentration 50 μg/mL) and further incubated for 30 minutes (or 1 h for M. tuberculosis) with gentamicin to kill extracellular bacteria. Drugs were diluted in DMEM and 10 FBS % to the desired concentrations. Subsequently, after washing, wells were treated with 100 μL of DMEM and 10% FBS containing drugs for 9 h (*S. enteritidis* and *S. flexneri*), 12 h (*M. smegmatis*), 21 h (*B. abortus*) and 7 days (*M. tuberculosis*). Ciprofloxacin (5 μM) was used as a positive control for *S. enteritidis* and *B. abortus*, and isoniazid (0.12 μM) for *M. tuberculosis* and *M. smegmatis*. Medium alone used as a negative control. After incubation, the media was aspirated and the wells were washed twice with PBS. Then 100 μL of PBS with 0.01% triton X was added to each well to lyse the macrophage cells. Subsequently, bacteria were diluted 10 fold serially in PBS and plated on Tryptic Soy Agar (TSA) plates (*M. tuberculosis* was plated on Middlebrook 7H10 Agar plates supplemented with OADC Enrichment). Plates were incubated at 37° C. for 20 h (*S. enteritidis* and *S. flexneri*), 48 h (*B. abortus*), 72 h (*M. smegmatis*) and 4-5 weeks (*M. tuberculosis*). After incubation, bacteria were counted and analyzed by Graph pad software. Each drug treatment was done with three biological replicates. Experiments were repeated independently twice except *M. tuberculosis* was done once with three biological replicates.

Antimicrobial Efficacy of Treatment In Vivo Using a *Salmonella*-Infected *C. Elegans* Animal Model.

The infection and treatment of *Caenorhabditis elegans* were performed as reported previously. See Alajlouni, R A, Seleem M N. Targeting *listeria monocytogenes* rpoA and rpoD genes using peptide nucleic acids. Nucleic acid therapeutics, 2013, 23, 363-7. A pathogen sensitive strain of *C. elegans* {glp-4(bn2) I; sek-1(km4)} was used in this study. Bacterial lawns used for the *C. elegans* infection assays were prepared by spreading 200 μL of the overnight culture of *Salmonella enteritidis* on the modified Nematode Growth Media (NGM) (0.35% peptone) agar plates. The plates were incubated at 37° C. overnight before being seeded with young adult hermaphrodite nematodes, grown at 25° C., from a synchronized culture. The infections were performed at 25° C. for 24 h. Subsequently, the worms were collected and washed with PBS to remove extracellular bacteria and diluted to reach 1 worm per 1 μL of PBS. Approximately 100 worms (100 μL PBS) were transferred to 1.5 mL microcentrifuge tubes. Drugs at concentration equal to 50 μM (except ciprofloxacin 10 μM) were added to tubes in triplicates. Control negative tubes contain only PBS. After 24 h, worms were checked for survival under a microscope to assess the toxicity of drugs. The tubes were centrifuged and the supernatant was removed. Worms were washed twice with 1 ml of PBS then 200 μg of autoclaved silica carbide were added to each tube, and the worms were vortexed for 1 minute at high speed. One hundred microliter from each tube was diluted 10 fold serially in PBS. Bacteria were plated in Tryptic Soy Agar (TSA) plates containing spectinomycin (18 μg/mL) to allow for selective growth of *S. enteritidis* over *Escherichia coli*. Plates were incubated for 16 h at 37° C. and colonies were counted. Statistical analysis was analyzed by two tailed student t test. (P≤0.05 was considered significant).

Method for In Vivo Toxicity Assessment in *C. elegans* Animal Model

Bacterial lawns used for *C. elegans* infection assays were prepared by spreading 200 ul of the overnight culture of biofilm strains of *S. aureus* or *S. epidermidis* on modified NGM (0.35% peptone) agar plates. The plates were incubated at 37° C. overnight before being seeded with young adult hermaphrodite nematodes, grown at 25° C., from a synchronized culture. The infections were performed at 25° C. for 12 hours. After infection of synchronized worms, around 25-30 adult worms were transferred to each well in 96 well plate, Drugs at concentration equal to 50 μM were added in triplicates. Control negative contains only PBS. Worms were checked for survival under microscope at different time points. Living nematodes maintain a sinusoidal shape, whereas dead nematodes appear as straight, rigid rods as the corpse becomes filled with bacteria.

Encouraged by the potent antibacterial activity of the peptide conjugate Example 1 in vitro and in the in cyto bacterial clearing assay, it was investigated the ability of the conjugate to clear *S. enteritidis* using an in vivo *C. elegans* model. First the toxicity of Example 1, P14LRR, kanamycin and melittin at 50 μM against *C. elegans* were evaluated. After 3 days of treatment with Example 1, P14LRR or kanamycin the *C. elegans* were highly viable (>90%), whereas no live worms were observed with melittin after this time. These data suggested the non-toxic nature of the kanamycin-peptide conjugate. To monitor antibacterial activity, *S. enteritidis* infected *C. elegans* were treated with a range of concentrations of Example 1, P14LRR, kanamycin, and a 1:1 mixture of P14LRR and kanamycin for 24 hr, and the bacteria levels were monitored. Example 1 demonstrated significantly reduced levels of *Salmonella* inthe *C. elegans* host as compared to the 1:1 mixture of antibiotics across all concentrations, and at the highest dose approximately 90% of the bacteria had been cleared in vivo. The *C. elegans* infection model confirms that Example 1 does exhibit potent in vivo antimicrobial activity and has significant promise to be used as a novel treatment of intracellular pathogens.

Method for Leakage of β-Galactosidase from *E. coli* Treated with Example 1

In a sterile 250 mL erlenmeyer flask *E. coli* (ATCC 25922) was grown to mid-exponential phase (OD590≈0.6) in TSB (~50 mL) at 37° C. with shaking. β-Galactosidase expression was induced by the addition of freshly prepared isopropyl-β-D-thiogalactopyranoside (IPTG) (Gold Biotechnology I2481C5) in PBS (1 mM final concentration). A 4 mL aliquot of the bacterial suspension was centrifuged, washed twice with fresh TSB and plated into a sterile 96-well plate (90 μL). Next, 10 μL aliquots of Example 1 in sterile water were added to give final concentrations of 10 μM. Bacteria treated with sterile water and melittin (40 μM final concentration) served as controls. The plate was then incubated for 1 h at 37° C. At the end of the incubation period, the plate was centrifuged at 3000 rpm at 4° C. for 10 min. 80 μL of the supernatant from each well was carefully transferred to a new sterile 96-well plate. Next, 20 μL of freshly prepared 2-Nitrophenyl-β-D-galactopyranoside (ONPG) (Sigma 73660) in PBS was added to each well (0.8 mg/ml final concentration). The β-Galactosidase activity was monitored at $OD_{405}$ every five minutes for a period of 1 h using a micro-plate reader. Data was obtained in duplicates from at least two independent experiments.

Anti-Inflammatory Effect of Compounds on LPS Stimulated Macrophages (Neutralizing the Effect of LPS on Macrophages).

The anti-inflammatory effect of compounds on LPS stimulated macrophages, J774A.1 cells was investigated. Next, the cells were stimulated with LPS (150 ng/ml final concentration) in the presence of 10 μM of compounds. Cells that were stimulated with LPS alone and untreated cells served as controls. Cells were incubated for six hours at 37° C. and supernatants from each treatment were collected and stored at −20° C. until use. Cytokine detection of tumor necrosis factor-α (TNF-α) and interleukin-6 (IL-6) in supernatants was done using ELISA as described before following the manufacturer's instructions[24,25]. Cytokine levels were expressed as percent change relative to the LPS-stimulated control, using triplicate samples for each treatment condition.

Example 1 and the peptide P14LRR were able to bind to LPS in vitro as evident by inhibition of the LPS-induced activation of the LAL enzyme (*Limulus* amoebocyte lysate). Example 1, P14LRR and colistin (a known LPS-binding agent) produced 60.8%±6.5, 71.2%±5 and 79.76%±4.6 inhibition of the LAL enzyme at 10 µM, respectively. However, kanamycin demonstrated only minimal inhibition (6.9%±3.5) at the same concentration.

Example 1 and P14LRR were able to inhibit LPS-induced proinflammatory cytokines in macrophages in a manner similar to colistin. Example 1, P14LRR and colistin, at 10 µM, decreased TNF-α levels by 65.53%±2.45, 68.4%±5.43, 97.53%±0.32, respectively; and IL-6 levels by 74.71%±9.10, 81.92%±0.78 and 95.04%±0.56%, respectively. Kanamycin, in contrast, produced an 11.41%±4.5 and 10%±3.30 inhibition of TNF-α and IL-6 levels, respectively. The capability of Example 1 to reduce endotoxin-mediated proinflammatory cytokine production provides a potential avenue for its development as an antibacterial agent to treat sepsis and also as an adjunctive with antibiotics to overcome sepsis.

Efficacy of Compounds on Bacterial Biofilms

The compounds of the present disclosure were examined for their ability to disrupt bacterial biofilms using the microtiter dish biofilm formation assay. Briefly, overnight cultures of *S. aureus* (ATCC 6538) and *S. epidermidis* (ATCC 35984) were diluted 1:100 in TSB supplemented with 1% glucose. Overnight cultures of *P. aeruginosa* PAO1 and *A. baumannii* ATCC BAA-1605 were diluted 1:100 in M63 minimal medium supplemented with magnesium sulfate, glucose and casamino acids. Bacterial suspensions were incubated in 96-well plates at 37° C. for 24 hours. After removing media, wells were rinsed with PBS to remove planktonic bacteria before re-filling wells with fresh media. Compounds were added at specific concentrations and plates were incubated at 37° C. for 24 hours. After incubation, wells were washed and biofilms were stained with 0.5% (w/v) crystal violet for 30 minutes. The dye was solubilized with ethanol (95%) and the biofilm mass was quantified at $OD_{595}$. Experiments were done in triplicate and repeated twice independently.

Efficacy of P14KanS on Established Biofilms

Biofilms are aggregated bacterial communities covered by a polysaccharide matrix that protects bacteria from host immune defenses and hinders antibiotics from targeting deep-seated bacteria encased within the biofilm. Furthermore, biofilms act as an infectious niche with sustained release of bacteria inside the host that leads to disease relapses and therapy failure. Biofilm development has been linked to serious infections including pneumonia in cystic fibrosis patients, colonization of medical devices, and urinary tract infections. Biofilms pose a serious medical challenge that is difficult to control and there is a critical need to find agents that can address this problem. The capability of Example 1 and control antibiotics to disrupt established biofilms of four different bacterial isolates responsible for major biofilm infections—*S. aureus, S. epidermidis, P. aeruginosa* and *A. baumannii* were investigated. Example 1 disrupted mature (24 hour) biofilms more potently than several antibiotics of choice. Example 1 was superior to kanamycin and the peptide P14LRR against the kanamycin sensitive isolate (*S. aureus*). Example 1 demonstrated a concentration-dependent biofilm-disruptive activity. Example 1, at a low concentration (1 µM), disrupted more than 65% of the biofilm mass of *S. aureus* (p<0.05) whereas kanamycin and P14LRR were not effective at the same concentrations. At higher concentrations, Example 1 disrupted more than 75% and 82% of biofilm mass of *S. aureus*, at 4 and 8 µM, respectively, (p<0.05). Kanamycin, vancomycin and linezolid, at 8 µM, reduced approximately 50% of biofilm mass (p<0.05); whereas, P14LRR was not effective.

It was also investigated for the efficacy of Example 1 against biofilms of a clinical multidrug-resistant strain of *S. epidermidis* ATCC 35984, a high slime producing strain that was isolated from septicemic patients with colonized intravascular catheters in Tennessee, US. This strain is resistant to several antibiotics including methicillin, erythromycin, kanamycin, gentamicin, clindamycin and trimethoprim. The great thickness of the exopolysaccharide matrix of *S. epidermidis* biofilms cause it to become extremely resilient to penetration by antibiotics. Indeed, mature biofilms of *S. epidermidis* were less susceptible to vancomycin and linezolid even at 64 µM (equivalent to 64-128×MIC) where only 25-30% biofilm mass reduction was observed (FIG. 5b). However, Example 1 disrupted more than 30%, 50%, 70%, and 80% of biofilm mass at 8, 16, 32 and 64 µM, respectively, (P<0.05). The peptide alone, P14LRR, was ineffective except at 64 µM, disrupting approximately 50% of the biofilm mass. Kanamycin did not disrupt or reduce the biofilm mass of *S. epidermidis*.

Remarkably, Example 1 was capable of eradicating *P. aeruginosa* and *A. baumannii* biofilms at 32 µM, however, kanamycin was not effective. P14LRR (32 µM) was ineffective against *P. aeruginosa* biofilms and demonstrated only 30% reduction of *A. baumannii* biofilm mass. Collectively, the data demonstrate that Example 1 is superior to conventional antibiotics in penetrating and disrupting adherent biofilms of both Gram-positive and Gram-negative pathogens.

Example 1 exhibited potent antimicrobial activity against ESKAPE pathogens. Example 1 demonstrated a ≥128-fold improvement in MIC relative to kanamycin against kanamycin-resistant strains. Mechanistic studies confirmed that Example 1 exerts its antibacterial effect by selectively disrupting the bacterial cell membrane. Example 1 was not toxic or hemolytic at concentrations much higher than its MIC. Unlike many antibiotics, Example 1 demonstrated rapid bactericidal activity against stationary phases of both Gram-positive and Gram-negative pathogens. Furthermore, Example 1 was superior in disrupting adherent bacterial biofilms and in killing intracellular pathogens as compared to conventional antibiotics. It should be noted that Example 1 demonstrated potent anti-inflammatory activity via the suppression of LPS-induced proinflammatory cytokines. Finally, Example 1 protected *C. elegans* from lethal infections of both Gram-positive and Gram-negative pathogens.

Those skilled in the art will recognize that numerous modifications can be made to the specific implementations described above. The implementations should not be limited to the particular limitations described. Other implementations may be possible.

We claim:

1. A method of treating a microbial infection in a patient, wherein the method comprises administering to the patient a pharmaceutical composition comprising a compound of formula:

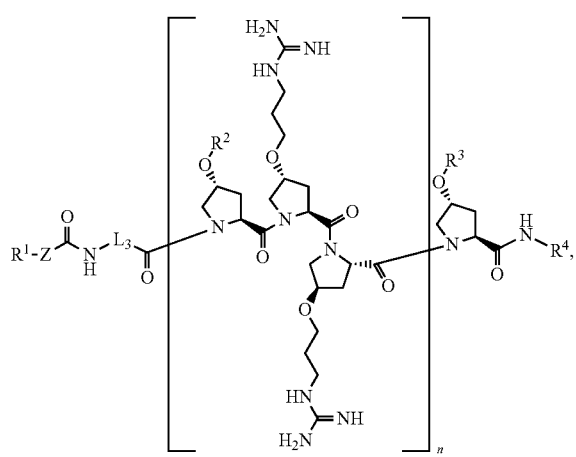

a stereoisomer, tautomer, solvate, pharmaceutically acceptable salt, or derivative thereof, wherein
- $R^1$ is an antibiotic moiety;
- $R^2$ and $R^3$ are each independently H, a $C_1$-$C_8$ branched or unbranched alkyl chain, or a $C_3$-$C_8$ cyclic alkyl;
- $R^4$ is H, a $C_1$-$C_8$ branched or unbranched alkyl chain, or a $C_3$-$C_8$ cyclic alkyl;
- $L_3$ is $C_1$-$C_8$ branched or unbranched alkyl chain, or a $C_3$-$C_8$ cyclic alkyl;
- Z is a linker comprising a disulfide bond (S—S bond); and
- n is 3-8, wherein the microbial infection is an infection caused by pathogen *S. aureus, S. epidermidis, P. aeruginosa, A. baumannii, K. pneumoniae, E. faecium*, enterobacteriaceae, or any combination thereof.

2. The method of claim 1, wherein the compound is:

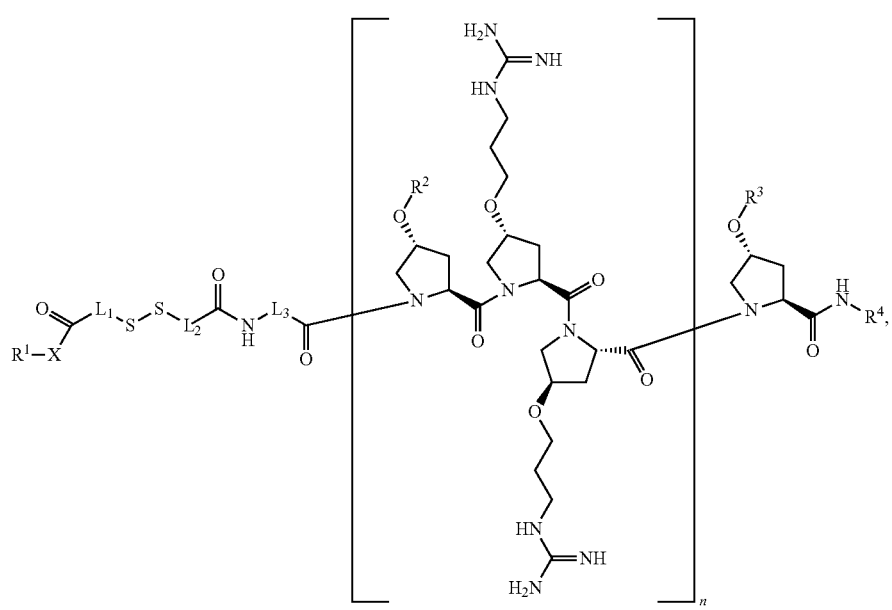

or a stereoisomer, tautomer, solvate, pharmaceutically acceptable salt, or derivative thereof, wherein
- $R^1$ is an antibiotic moiety;
- $R^2$ and $R^3$ are each independently H, a $C_1$-$C_8$ branched or unbranched alkyl chain, or a $C_3$-$C_8$ cyclic alkyl;
- $R^4$ is H, a $C_1$-$C_8$ branched or unbranched alkyl chain, or a $C_3$-$C_8$ cyclic alkyl;
- $L_1$, $L_2$, $L_3$ are each independently $C_1$-$C_8$ branched or unbranched alkyl chain, or a $C_3$-$C_8$ cyclic alkyl;
- X is O or $NR^5$, wherein $R^5$ is H, $C_1$-$C_8$ branched or unbranched alkyl chain, or a $C_3$-$C_8$ cyclic alkyl, or X combined with $R^1$ together is an antibiotic moiety; and
- n is 3-8.

3. The method of claim 1, wherein $R^1$ or $R^1$—X represents the moiety of an aminoglycoside antibiotics or any derivative thereof.

4. The method of claim 1, wherein $R^1$ or $R^1$—X represents an antibiotic moiety, wherein the antibiotic moiety is of an antibiotics selected from the group consisting of Gentamicin, Streptomycin, Kanamycin, Fradiomyctn, Paromomycin, Tobramycin, Netilmicin, Amikacin, Neomycin, Ribostamycin, Dibekacin, Sisomicin, Isepamicin, Bekanamycin, Astromicin, Plazomicin, Vancomycin, Linezolid, Erythromycin, Eperezolid, and any derivative thereof.

5. The method of claim 1, wherein $R^2$ and $R^3$ are each independently $C_1$-$C_4$ branched or unbranched alkyl chain.

6. The method of claim 1, wherein $R^2$ and $R^3$ are isobutyl group.

7. The method of claim 1, wherein $R^4$ is hydrogen.

8. The method of claim 2, wherein $L_1$ is —$(CH_2)_3$—, $L_2$ is —$(CH_2)_3$—, and $L_3$ is —$(CH_2)$—.

9. The method of claim 1, wherein $R^1$ represents an antibiotic moiety, and the antibiotic moiety is of an antibiotics selected from the group consisting of Gentamicin, Streptomycin, Kanamycin, Fradiomyctn, Paromomycin, Tobramycin, Netilmicin, Amikacin, Neomycin, Ribostamycin, Dibekacin, Sisomicin, Isepamicin, Bekanamycin, Astromicin, Plazomicin, Vancomycin, Linezolid, Erythromycin, Eperezolid, and any derivative thereof; $R^2$ and $R^3$ are isobutyl group; $R^4$ is hydrogen; $L_1$ is —$(CH_2)_3$—, $L_2$ is —$(CH_2)_3$—, and $L_3$ is —$(CH_2)$—; X is O; and n is 4.

10. The method of claim 2, wherein $R^1$ or $R^1$—X represents an aminoglycoside antibiotics moiety, and the aminoglycoside antibiotics is selected from the group consisting of Gentamicin, Kanamycin, Tobramycin, Amikacin, Neomycin, Plazomicin, and any derivative thereof; $R^2$ and $R^3$ are isobutyl group; $R^4$ is hydrogen; $L_1$ is —$(CH_2)_3$—, $L_2$ is —$(CH_2)_3$—, and $L_3$ is —$(CH_2)$—; X is O; and n is 4.

11. The method of claim 2, wherein $R^1$ or $R^1$—X represents Kanamycin moiety or any derivative thereof; $R^2$ and $R^3$ are isobutyl group; $R^4$ is hydrogen; $L_1$ is —$(CH_2)_3$—, $L_2$ is —$(CH_2)_3$—, and $L_3$ is —$(CH_2)$—; X is O; and n is 4.

12. The method of claim 1, wherein the compound is:

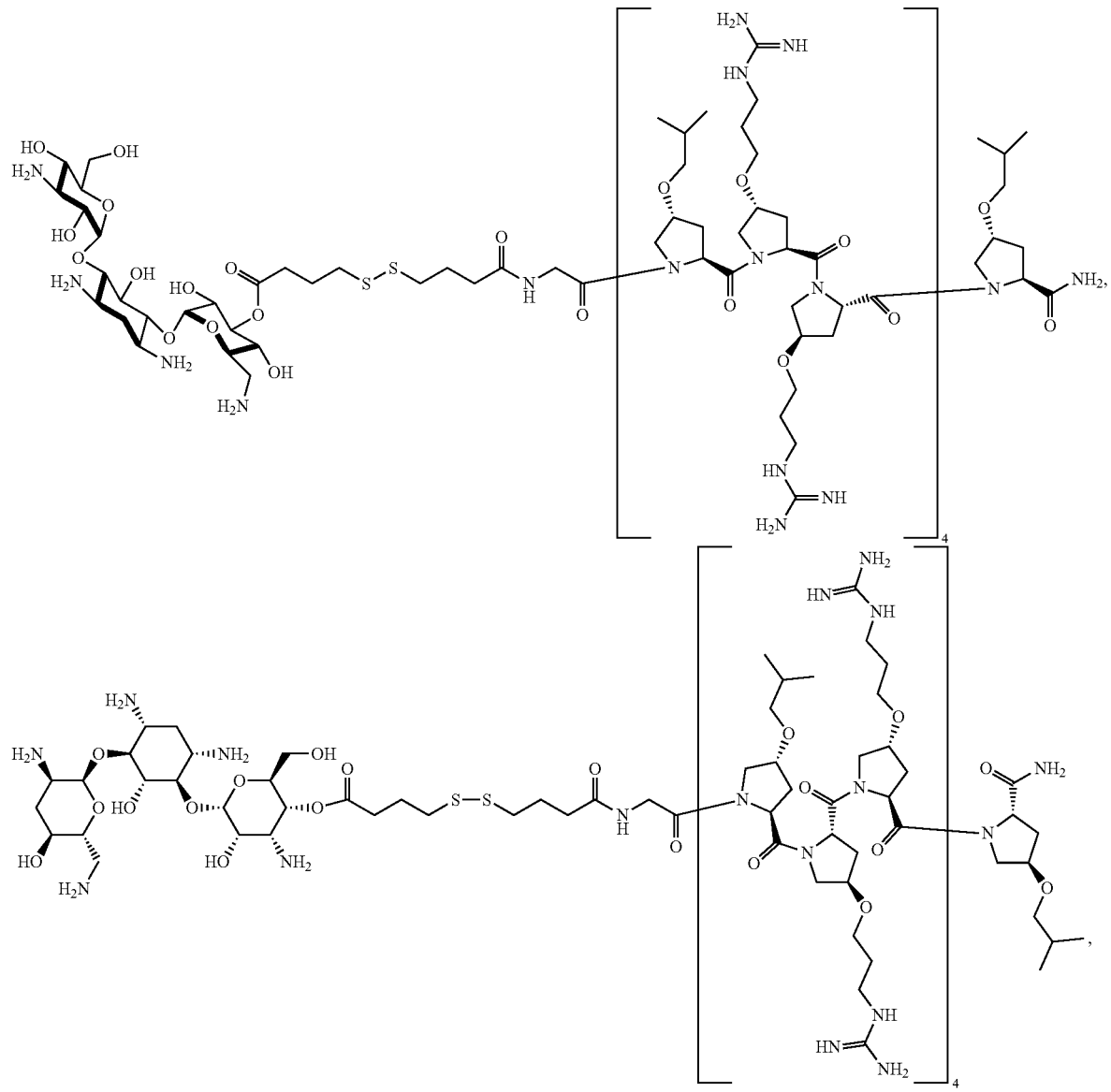

a stereoisomer, tautomer, solvate, pharmaceutically acceptable salt, or a derivative thereof.

13. The method of claim 1, wherein the microbial infection is a biofilm infection.

14. The method of claim 1, wherein the microbial infection is an infection caused by pathogen S. aureus (ATCC 6538), S. aureus (USA400), S. epidermidis (ATCC 35984), P. aeruginosa (PAO1), P. aeruginosa (1109), A. baumannii (BAA-1605), K. pneumoniae (BAA-1706), E. faecium (ATCC 700221) or any combination thereof.

* * * * *